(12) United States Patent
Rondinone et al.

(10) Patent No.: US 9,127,295 B2
(45) Date of Patent: Sep. 8, 2015

(54) MICROBIAL-MEDIATED METHOD FOR METAL OXIDE NANOPARTICLE FORMATION

(75) Inventors: Adam J. Rondinone, Knoxville, TN (US); Ji Won Moon, Oak Ridge, TN (US); Lonnie J. Love, Knoxville, TN (US); Lucas W. Yeary, Painted Post, NY (US); Tommy J. Phelps, Knoxville, TN (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 1184 days.

(21) Appl. No.: 12/357,523

(22) Filed: Jan. 22, 2009

(65) Prior Publication Data

US 2010/0184179 A1    Jul. 22, 2010

(51) Int. Cl.
  *C12P 3/00*    (2006.01)
  *B82Y 5/00*    (2011.01)
  *B82Y 40/00*    (2011.01)

(52) U.S. Cl.
  CPC ... *C12P 3/00* (2013.01); *B82Y 5/00* (2013.01); *B82Y 40/00* (2013.01)

(58) Field of Classification Search
  CPC .............. B82Y 40/00; B82Y 5/00; C12P 3/00
  USPC ........................................................ 435/168
  See application file for complete search history.

(56) References Cited

U.S. PATENT DOCUMENTS

| | | | |
|---|---|---|---|
| 4,954,231 A * | 9/1990 | Correia et al. ............. | 204/157.6 |
| 6,444,453 B1 | 9/2002 | Lauf et al. | |
| 7,060,473 B2 | 6/2006 | Phelps et al. | |
| 2002/0187889 A1 | 12/2002 | Lauf et al. | |
| 2006/0014261 A1 | 1/2006 | Phelps et al. | |
| 2008/0108749 A1* | 5/2008 | Chen ............................ | 524/795 |
| 2010/0193752 A1 | 8/2010 | Phelps et al. | |
| 2010/0330367 A1 | 12/2010 | Phelps et al. | |

OTHER PUBLICATIONS

Moon, et al, 2007. Microbial preparation of metal-substituted magnetite nanoparticles. Journal of Microbiological Methods 70: 150-158.*

Vasconcelos, et al, 1998. Copper(II) Complexation Properties and Surfactant Activity of 3-[N,N-Bis(2-hydroxyethyl)amino]-2-hydroxypropanesulfonic Acid and N-(2-Hydroxyethyl)piperazine-N9-2-hydroxypropanesulfonic Acid pH Buffers Which May Affect Trace Metal Speciation in in Vitro Studies. Analytical Biochemistry 265, 193-201.*
Limbach et al. Environ. Sci. Technol. 2008, 42, 5828-5833.*
Love L.J., et al. "Characterization of Bio-Synthesized Magnetic Nanoparticles", *Proceedings of the 2005 IEEE/ASME International Conference on Advanced Intelligent Mechatronics*, Monterey, California (Jul. 24-28, 2005).
Roh V. et al. "Isolation and Characterization of Metal-Reducing *Thermoanaerobacter* Strains from Deep Subsurface Environments of the Piceance Basin, Colorado", *Applied and Environmental Microbiology*, 68(12): 6013-6020 (Dec. 2002).
Rondinone A.J. et al., "A Chemometric Approach for Predicting the Size of Magnetic Spinel Ferrite Nanoparticles from the Synthesis Conditions", *J. Phys. Chem. B*, 104(33):7919-7922 (2000).
Kieft T.L. et al., "Dissimilatory Reduction of Fe(III) and Other Electron Acceptors by a *Thermus* Isolate", *Applied and Environmental Microbiology* 65(3):1214-1221 (1999).
Bowman J.P. et al., "*Shewanella gelidimarina* Sp. Nov. and *Shewanella frigidimarina* Sp. Nov., Novel Antarctic Species With the Ability to Produce Eicosapentaenoic Acid (20:5ω3) and Grow Anaerobically by Dissimilatory Fe(III) Reduction", *International Journal of Systematic Bacteriology* 47(4):1040-1047 (1997).
Lovley D.R. et al., "*Geobacter metallireducens* Gen. Nov. Sp. Nov., a Microorganism Capable of Coupling the Complete Oxidation of Organic Compounds to the Reduction of Iron and Other Metals", *Arch. Microbiol.* 159:336-344 (1993).
Official Action dated Aug. 29, 2013 in U.S. Appl. No. 12/364,638.

* cited by examiner

*Primary Examiner* — Janet Epps-Smith
(74) *Attorney, Agent, or Firm* — Scully, Scott, Murphy & Presser, P.C.

(57) ABSTRACT

The invention is directed to a method for producing metal oxide nanoparticles, the method comprising: (i) subjecting a combination of reaction components to conditions conducive to microbial-mediated formation of metal oxide nanoparticles, wherein said combination of reaction components comprise: metal-reducing microbes, a culture medium suitable for sustaining said metal-reducing microbes, an effective concentration of one or more surfactants, a reducible metal oxide component containing one or more reducible metal species, and one or more electron donors that provide donatable electrons to said metal-reducing microbes during consumption of the electron donor by said metal-reducing microbes; and (ii) isolating said metal oxide nanoparticles, which contain a reduced form of said reducible metal oxide component. The invention is also directed to metal oxide nanoparticle compositions produced by the inventive method.

21 Claims, 5 Drawing Sheets

MICROBIAL-MEDIATED METHOD FOR METAL OXIDE NANOPARTICLE FORMATION

This invention was made with government support under Contract Number DE-AC05-00OR22725 between the United States Department of Energy and UT-Battelle, LLC. The United States government has certain rights in this invention.

FIELD OF THE INVENTION

The present invention relates to the field of microbial synthesis of inorganic materials, and more particularly, wherein the inorganic materials are metal oxide nanoparticles.

BACKGROUND OF THE INVENTION

Nanoparticles having metal oxide compositions are increasingly being used in numerous emerging applications. Some of these include the use of magnetic nanoparticles (e.g., magnetite) in magnetic refrigeration or magnetic cooling circuits Ferrite-type nanoparticles, in particular, are being intensely studied for their use in the fields of biomedicine, optics, and electronics.

Current methods for the production of nanoscale ferrites and other oxide ceramics generally entail calcining a precursor (e.g., a carbonate) at a high temperature, and then mechanical milling the calcined product to reduce the particle size. The process is energy and time intensive, generally difficult to control, and often requires several repetitions of the process before a final product is obtained.

Chemical processes, such as precipitation and sol-gel techniques, are also known for the production of metal oxide nanoparticles. However, these processes are typically more expensive than mechanical milling, and also generally highly limited with respect to size or shape control of the resulting particles. Often, a chemical or physical reduction step is needed to convert a metal oxide precursor to a metal oxide product. In addition, these processes often require a mechanical milling step to break up agglomerates formed during the reduction process.

The microbial synthesis of metal oxide nanoparticles is known. See, for example, U.S. Pat. Nos. 6,444,453 and 7,060,473. However, there are significant problems in the microbial process as currently practiced. For example, there is the difficulty of obtaining pure nanoparticle product bereft of microbial matter. Therefore, numerous lysing or washing steps are often required. There is also the difficulty in controlling the particle size or the morphology of the nanoparticles.

In order to make microbial synthesis of metal oxide nanoparticles a more convenient and commercially viable method, the microbial process is in need of an improvement whereby substantially pure nanoparticle product bereft of microbial matter can be obtained upon precipitation from microbes. There is also a need for a microbial process whereby the particle size and/or morphology of the nanoparticles can be controlled during microbial synthesis of the nanoparticles.

SUMMARY OF THE INVENTION

The present invention is directed to a microbial-mediated method for the production of metal oxide nanoparticles. Specifically, the method involves the inclusion of one or more surfactants in the synthetic process in order to facilitate separation of the nanoparticles from the microbes. The surfactant-induced separation also facilitates precipitation of the nanoparticles and results in a highly purified form thereof. The surfactant also advantageously permits the particle size and/or morphology of the nanoparticles to be controlled.

In a preferred embodiment, the method involves: (i) subjecting a combination of reaction components to conditions conducive to microbial-mediated formation of metal oxide nanoparticles, wherein said combination of reaction components include: metal-reducing microbes, a culture medium suitable for sustaining said metal-reducing microbes, an effective concentration of one or more surfactants, a reducible metal oxide component containing one or more reducible metal species, and one or more electron donors that provide donatable electrons to the metal-reducing microbes during consumption of the electron donor by the metal-reducing microbes; and (ii) isolating said metal oxide nanoparticles, which contain a reduced form of said reducible metal oxide component.

Thus, as will be described in further detail below, the method advantageously provides a microbial-mediated synthesis of metal oxide nanoparticles wherein the microbial process is economical, convenient, and environmentally friendly. The method also provides substantially pure nanoparticle product bereft of microbial matter after precipitation from metal-reducing microbes. In addition, the method permits the particle size and/or morphology of the nanoparticles to be controlled.

DETAILED DESCRIPTION OF THE INVENTION

Figure 1:
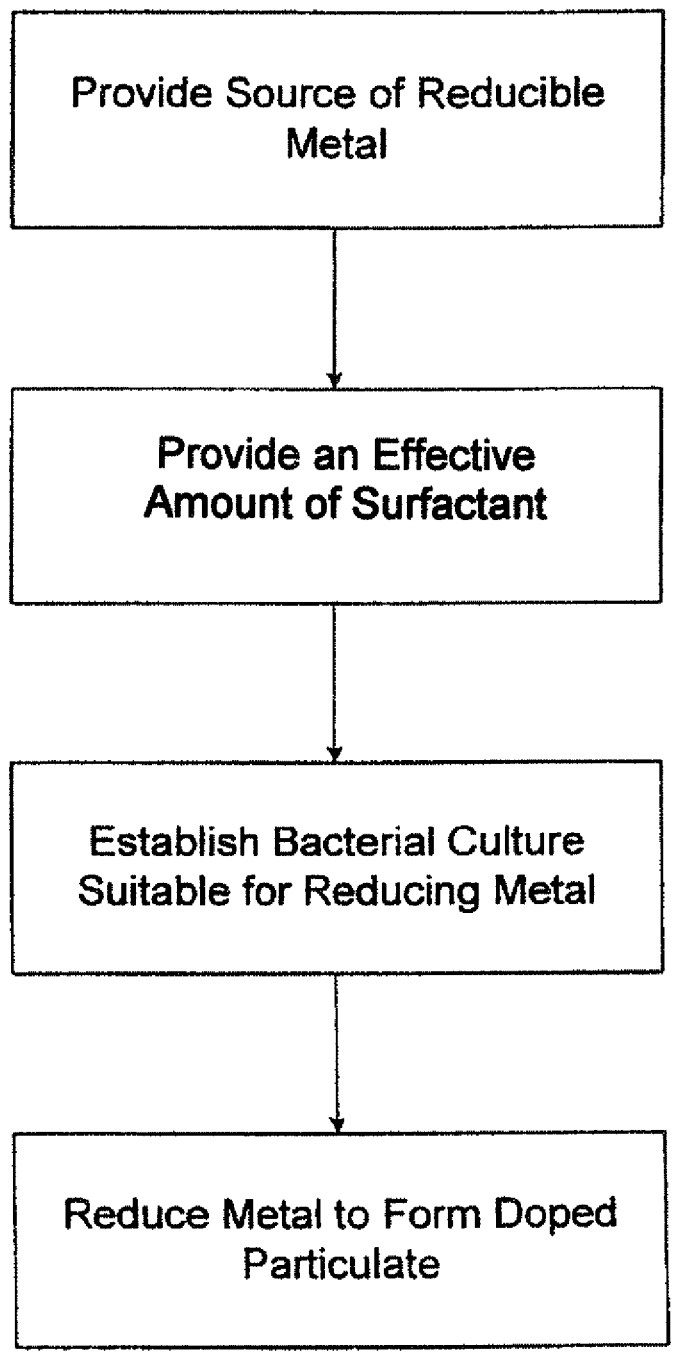
FIG. 1. A process diagram illustrating a preferred embodiment of the invention for forming mixed constituent crystalline phase nanoparticles.

According to the invention, a reducible metal oxide component (i.e., nanoparticle precursor) is transformed into metal oxide nanoparticles by metal-reducing microbes. The reducible metal oxide component contains, minimally, one or more reducible metal ions and oxygen atoms. In one embodiment, at least a portion of the reducible metal oxide component contains an oxide structure (i.e., —O— linkages between metal ions). In another embodiment, the reducible metal oxide component does not contain —O— linkages, but rather, oxygen-containing groups, such as hydroxide (e.g., $Fe(OH)_3$), nitrate, nitro, chlorate, perchlorate, peroxide, superoxide, carbon monoxide, or metal-oxo (unlinked) groups. In yet another embodiment, the reducible metal oxide component contains —O— linkages in combination with any of the foregoing groups.

In one embodiment, the reducible metal oxide component contains only metal-O-metal links, except that a minor portion of hydroxy groups (e.g., up to 10% by weight) may be present. Such a composition can be considered a pure metal oxide composition. Pure metal oxides not in salt form (e.g., $Fe_2O_3$ or $CrO_3$) are typically insoluble in water, and thus, are more typically used as finely divided aqueous suspensions. On the contrary, pure metal oxides in salt form (e.g., the chromates, dichromates, and permanganates) are generally soluble in water, and thus, are typically used as aqueous solutions.

In another embodiment, the reducible metal oxide component contains the metal-O-metal links along with a significant portion of other oxygen-containing chemical groups, e.g., hydroxy groups (above 10% by weight), phosphate, nitrate, carbonate, citrate, acetate, or other groups. For example, the reducible metal oxide component can be the magnetite precursor Fe(III) oxyhydroxide generally prepared in situ by mixing an Fe(III) halide with a hydroxide base.

As used herein, the term "metal oxide" indicates compounds or materials containing at least one metal species and oxide atoms, and the term "mixed metal oxide" indicates compounds or materials containing at least two different metal species and oxide atoms. When more than one metal is included, the metals may be substantially intermixed throughout the reducible metal oxide component such that separate phases do not exist. Alternatively, the different metals may form distinct phases composed of different metal oxide compositions in the reducible metal oxide component. The metal oxide compounds or materials may further contain chemisorbed water, water of hydration, or adsorbed molecular groups.

The reducible metal oxide component contains at least one metal capable of being reduced by a metal-reducing microbe. The one or more reducible metals can be any of the metals of the Periodic Table of the Elements having this ability. Preferably, the one or more reducible metals are transition metals, i.e., Groups III-XII (scandium through zinc groups). More preferably, the one or more reducible metals are first-row transition metals. Some examples of reducible first-row transition metal ions include Sc(III), Ti(IV), V(III), Cr(VI), Cr(III), Mn(VII), Mn(V), Mn(IV), Mn(III), Fe(III), Co(III), Ni(III), and Cu(II).

In one embodiment, the reducible metal oxide component contains a single metal. The reducible metal oxide component can be, for example, an oxide, oxyhydroxide, or hydroxide of any one of the reducible metals described above. In another embodiment, the reducible metal oxide component contains more than one metal. For example, the reducible metal oxide component can be composed of two reducible metals (e.g., Fe(III) and Co(III), or Fe(III) and Cr(VI)), or three reducible metals (e.g., Fe(III), Co(III), and Cr(VI)), or a reducible metal and a non-reducible metal (e.g., Fe(III) and Zn(II), or Ti(IV) and Al(III), or U(VI) and Fe(II), or Fe(II) and Fe(III)), or two or more reducible metals and a non-reducible metal, or a reducible metal and two or more non-reducible metals, or two or more reducible metals and two or more non-reducible metals. As used herein, the term "non-reducible metal" is a metal not capable of being reduced by metal-reducing bacteria. Some examples of non-reducible metals include the alkali metals (e.g., $Li^+$, $Na^+$, and $K^+$), alkaline earth metals (e.g., $Mg^{2+}$, $Ca^{2+}$, and $Sr^{2+}$), main group elements (e.g., cations of Group IIIA-VIIA of the Periodic Table, such as $B^{3+}$ and $Al^{3+}$), and lower oxidation state transition metals (e.g., $Ti^{2+}$, $V^{2+}$, $Cr^{3+}$, $Mn^{2+}$, $Fe^{2+}$, $Co^{2+}$, $Ni^{2+}$, $Cu^{1+}$, $Zn^{2+}$). Depending on the conditions used, including the type of metal-reducing bacteria selected, a metal of intermediate oxidation state (e.g., $Mn^{4+}$) can be reducible or non-reducible.

In a particular embodiment, the reducible metal oxide component includes one or more Fe(III)-containing compounds or materials. Some examples of Fe(III)-containing compounds or materials include the iron(III) halides (e.g., $FeCl_3$), nitrates, hydroxides, oxides, oxidehydroxides (also denoted herein as FeOOH, or Fe(O)OH), tungstates, titanates, chromates, vanadates, silicates, spinels (e.g., the ferrites), and perovskites. The Fe(III)-containing compound or material can also include a mixed-valence (e.g., Fe(II)-Fe(III)) portion. In particular, the Fe(III) oxidehydroxides can be any forms of these materials known in the art, e.g., goethite ($\alpha$-FeOOH), akageneite ($\beta$-FeOOH), lepidocrocite ($\gamma$-FeOOH), ferrihydrite ($Fe_5HO_8 \cdot 4H_2O$ or $5Fe_2O_3 \cdot 9H_2O$), Schwertmannite ($Fe_8O_8(OH)_6(SO_4) \cdot nH_2O$ or $Fe^{3+}_{16}O_{16}(OH,SO_4)_{12-13} \cdot 10\text{-}12H_2O$), or green rusts (e.g., $Fe^{III}_xFe^{II}_y(OH)_{3x+2y-z}(A^-)_z$; where $A^-$ is $Cl^-$ or $0.5\ SO_4^{2-}$), or a modified form or combination thereof. The Fe(III) oxides are typically accordingly to the general formula $Fe_2O_3$ (generally, hematite), and can be in any crystalline or amorphous phase thereof Some examples of hematite phases include $\alpha$-$Fe_2O_3$ (hematite proper), $\beta Fe_2O_3$, $\gamma$-$Fe_2O_3$ (maghemite), and $\epsilon$-$Fe_2O_3$.

When one or more non-reducible metal species are included in the precursor composition, they typically become incorporated into the final metal oxide nanoparticle to some extent. Typically, the non-reducible metal species are included in the same weight or molar basis as provided in the precursor composition.

The molar ratio of metal ions in the precursor composition can be adjusted such that a particular molar ratio of metals is provided in the nanoparticle product. Typically, the molar ratio of metal ions in the precursor composition is the molar ratio of metals found in the nanoparticle product. However, the molar ratio of metals in the product may, in several embodiments, differ from the molar ratio of metals in the precursor composition. In a particular embodiment, a desired molar ratio of metals is achieved in the nanoparticle product by suitable adjustment of metal ratios in the precursor composition.

The total metal concentration should be below a concentration at which the metals are toxic to the microbes being used. Typically, the total metal concentration is no more than 100 mM. In different embodiments, the total metal concentration may preferably be no more than 90 mM, 80 mM, 70 mM, 60 mM, 50 mM, 40 mM, 30 mM, 20 mM, 15 mM, 10 mM, 5 mM, 1 mM, 0.5 mM, or 0.1 mM, or within a range resulting from any two of the above exemplary values.

The metal-reducing microbes can be any microbes known in the art capable of reducing one or more metal ions. In a particular embodiment, at least a portion of the metal-reducing microbes are Fe(III)-reducing microbes. The microbe can be, for example, eukaryotic or procaryotic, and either unicellular or multicellular. Of particular relevance herein are the procaryotic organisms, which are predominantly unicellular, and are divided into two domains: the bacteria and the archaea. Both metal-reducing bacteria and archaea are considered herein, though the microbes predominantly being considered herein are bacteria.

In one embodiment, the metal-reducing microbes considered herein are thermophilic, i.e., those organisms capable of thriving at temperatures of at least about 40° C. (and more typically, at least 45° C. or 50° C.) and up to about 100° C. or higher temperatures. Preferably, the thermophilic microbes are either bacteria or archaea, and particularly, those possessing an active hydrogenase system linked to high energy electron carriers. In a particular embodiment, at least a portion of the thermophilic microbes are Fe(III)-reducing microbes.

A group of thermophilic bacteria particularly considered herein are the species within the genus *Thermoanaerobacter*. A particular species of *Thermoanaerobacter* considered herein is *Thermoanaerobacter ethanolicus*, particularly strain TOR-39, a sample of which was deposited with the American Type Culture Collection (10801 University Blvd., Manassas, Va. 20010) on Sep. 7, 2001 as accession number PTA-3695. Strain TOR-39 is a thermophile that grows optimally at temperatures from about 65 to 85° C. The conditions needed to grow and maintain this strain, including basal medium, nutrients, vitamins, and trace elements are detailed in U.S. Pat. No. 6,444,453, the entire contents of which are incorporated herein by reference. Some particular strains of *Thermoanaerobacter ethanolicus* particularly considered herein include *T. ethanolicus* strain C1 and *T. ethanolicus* strain M3.

Another group of thermophilic bacteria particularly considered herein are the species within the class Thermococci. An order of Thermococci particularly considered herein is Thermococcales. A family of Thermococcales particularly considered herein is *Thermococcaceae*. A genus of *Thermococcaceae* particularly considered herein is *Thermococcus*. A species of *Thermococcus* particularly considered herein is *Thermococcus litoralis*.

Yet another group of thermophilic bacteria particularly considered herein are the species within the genus *Thermoterrabacterium*. A species of *Thermoterrabacterium* particularly considered herein is *Thermoterrabacterium ferrireducens*, and particularly, strain JW/AS-Y7.

Still another group of thermophilic bacteria particularly considered herein are the species within the phylum *Deinococcus-Thermus*. A class of *Deinococcus-Thermus* particularly considered herein is Deinococci. An order of Deinococci particularly considered herein is Thermales. A genus of Thermales particularly considered herein is *Thermus*. A species of *Thermus* particularly considered herein is *Thermus* sp. strain SA-01.

Other thermophilic bacteria particularly considered herein are the species within the genus *Thermoanaerobacterium*, and *Bacillus infernus*.

In another embodiment, the metal-reducing microbes considered herein are mesophilic (e.g., organisms thriving at moderate temperatures of about 15-40° C.) or psychrophilic (e.g., organisms thriving at less than 15° C.). As used herein, the term "psychrophilic" also includes "psychrotolerant". Psychrophilic bacteria are typically found in deep marine sediments, sea ice, Antarctic lakes, and tundra permafrost. In a particular embodiment, at least a portion of the mesophilic or psychrophilic microbes are Fe(III)-reducing microbes. Some examples of such bacteria include *Shewanella alga* strain PV-1, *Shewanella alga*, PV-4, *Shewanella pealeana*, W3-7-1, *Shewanella gelidimarina*, and *Shewanella frigidimarina*. Other examples of mesophilic or psychrophilic bacteria include those in the genera *Clostridium* (e.g., *Clostridium frigoris*, *Clostridium lacusfryxellense*, *Clostridium bowmanii*, *Clostridium psychrophilum*, *Clostridium laramiense*, *Clostridium estertheticum*, and *Clostridium schirmacherense*), *Bacillus* (e.g., *Bacillus psychrosaccharolyticus*, *Bacillus insolitus*, *Bacillus globisporus*, *Bacillus psychrophilus*, *Bacillus cereus*, *Bacillus subtilis*, *Bacillus circulans*, *Bacillus pumilus*, *Bacillus macerans*, *Bacillus sphaericus*, *Bacillus badius*, *Bacillus lichenzformis*, *Bacillus firmus*, *Bacillus globisporus*, and *Bacillus marinus*), and Geobacter (e.g., *Geobacter bemidjiensis* and *Geobacter psychrophilus*).

In yet another embodiment, the metal-reducing microbes considered herein are dissimilatory iron-reducing bacteria. Such bacteria are widely distributed and include some species in at least the following genera: *Bacillus, Deferribacter, Desulfuromonas, Desuluromusa, Ferrimonas, Geobacter, Geospirillum, Geovibrio, Pelobacter, Sulfolobus, Thermoanaerobacter, Thermoanaerobium, Thermoterrabacterium,* and *Thermus*.

The microbes used in the method described herein can be obtained and cultured by any of the methods known in the art. Some of the general processes by which metal-reducing bacteria may be used is taught in U.S. Pat. Nos. 6,444,453 and 7,060,473, the entire disclosures of which are incorporated herein by reference. The isolation, culturing, and characterization of thermophilic bacteria are described in, for example, T. L. Kieft et al., "Dissimilatory Reduction of Fe(III) and Other Electron Acceptors by a *Thermus* Isolate," *Appl. and Env. Microbiology*, 65 (3), pp. 1214-21 (1999). The isolation, culture, and characterization of several psychrophilic bacteria are described in, for example, J. P. Bowman et al., "*Shewanella gelidimarina* sp. nov. and *Shewanella frigidimarina* sp. nov., Novel Antarctic Species with the Ability to Produce Eicosapentaenoic Acid (20:5ω3) and Grow Anaerobically by Dissimilatory Fe(III) Reduction," *Int. J. of Systematic Bacteriology* 47 (4), pp. 1040-47 (1997). The isolation, culture, and characterization of mesophilic bacteria are described in, for example, D. R. Lovley et al., "*Geobacter metallireducens* gen. nov, sp. nov., a microorganism capable of coupling the complete oxidation of organic compounds to the reduction of iron and other metals," *Arch. Microbiol.*, 159, pp. 336-44 (1993). The disclosures of the above references are incorporated herein by reference in their entirety.

Without being bound by any theory, it is believed that the metabolic process in thermophilic bacteria that results in metal reduction generally involves a hydrogen ion ($H^+$)/electron donor and an oxidized metal ion (e.g., $Fe^{+3}$) acceptor. The electrons pass through one or more metabolic processes within the bacterial cell, providing energy for the bacterium. Ultimately, electrons are donated by the bacterial cell to a suitable electron acceptor such as Fe(III), reducing it to Fe(II).

For purposes of illustration, the discussion below focuses on the reduction of Fe(III) by thermophilic bacteria. However, the concepts may be applied to other metal species and other types of bacteria.

Starting with an aqueous solution at a pH of 8 and zero potential, any iron present will have a valence of +3, and a suspension of hydrous Fe(III) oxides will be stable. When thermophilic bacteria are added and provided with an electron donor source such as hydrogen, the hydrous Fe(III) oxides are typically converted to magnetite. The magnetite product phase typically contains equiaxed euhedral crystals (typically cubes, octahedra, or modified structures thereof) as are typical of spinel-type oxides. In magnetite, which may alternately be expressed as $FeO.Fe_2O_3$, ⅔ of the iron ions remain as Fe(III). Thus, it is theorized that the bacteria are not simply reducing Fe(III) to Fe(II), but are instead effectively moving the electrochemical potential of the system into the region where magnetite is the stable phase. When all of the Fe(III) oxyhydroxide has been converted to magnetite, bacterial respiration ceases because the electrochemical potential of magnetite is such that it is not a usable electron acceptor in the bacterial system.

If one starts with a source of aqueous ferric ions such as FeO(OH) and adds an electron donor such as hydrogen (for example, by bubbling gaseous hydrogen through the solution) the equilibrium potential of the system initially lowers to some point at which Fe(II) becomes stable. However, this only implies that the following reaction is thermodynamically favored:

$$3FeO(OH) + \tfrac{1}{2}H_2 \rightarrow Fe_3O_4 + 2H_2O$$

Kinetic limitations effectively prevent a significant amount of product to be formed from this reaction at temperatures ranging from ambient to about 65° C.

When iron-reducing bacteria are added, the reaction proceeds to completion with substantially all FeO(OH) being converted to $Fe_3O_4$. Thus, in a sense, the bacteria may be considered a catalyst that facilitates the kinetics of the above reaction. In contrast to a chemical catalyst, the bacteria extract some metabolic energy to survive, so the equilibrium potential of the entire assemblage is slightly higher than it would be with the electron donor present but no bacteria. The potential of the system is such that $Fe_3O_4$ is the stable phase, but now the reaction shown in the equation above is also kinetically favorable because of the crucial role played by bacterial respiration in splitting the hydrogen molecule and making electrons available at a suitable potential to reduce Fe(III) and form $Fe_3O_4$. Similar processes apply to other electron donors, such as lactate, pyruvate, formate, acetate, glucose, etc., for which overall reactions analogous to the one above can be written.

The culture medium for sustaining the microbes can be any of the known aqueous-based media known in the art useful for this purpose. The culture medium may also facilitate growth of the microbes. As is well known in the art, the culture medium includes such components as nutrients, trace elements, vitamins, and other organic and inorganic compounds, useful for the sustainment or growth of microbes.

In the method of the invention, the metal-reducing microbes are provided with at least one electron donor. An electron donor is any compound or material capable of being oxidatively consumed by the metal-reducing microbes such that donatable electrons are provided to the microbes by the consumption process. The produced electrons are used by the microbes to reduce one or more metal ions of the reducible metal oxide component.

In one embodiment, the electron donor includes one or more carboxylate-containing compounds that can be oxidatively consumed by the microbes. Some examples of suitable carboxylate-containing compounds include formate, acetate, propionate, butyrate, oxalate, malonate, succinate, fumarate, glutarate, lactate, pyruvate, glyoxylate, glycolate, and citrate.

In another embodiment, the electron donor includes one or more sugars (i.e., saccharides, disaccharides, oligosaccharides, or polysaccharides) that can be oxidatively consumed by the microbes. Some examples of suitable sugars include glucose, fructose, sucrose, galactose, maltose, mannose, arabinose, xylose, lactose, and disaccharides therefrom, oligosaccharides therefrom, or polysaecharides therefrom.

In another embodiment, the electron donor includes one or more inorganic species that can be oxidatively consumed by the microbes. The inorganic species can be, for example, an oxidizable gas, such as hydrogen or methane. Such gases can be oxidized by hydrogen-consuming or methane-consuming microbes which have the capacity to reduce one or more metals by the produced electrons.

The one or more surfactants (the surfactant component) used in the method are any compounds or materials that have an ability to associate with the surface of a metal-containing particle (i.e. are surface active). The surfactants are preferably water-soluble, either by being naturally water-soluble, or alternatively, by being rendered substantially water-soluble by the inclusion of one or more solubilizers (e.g., an alcohol) in the aqueous solution. The surfactants may also be partially soluble or substantially insoluble in water. If so, measures are taken to ensure that the surfactants contact the particles (e.g., by means of agitation or a transfer agent).

Many of the surfactants contain a hydrocarbon moiety and a functionalized (i.e., non-hydrocarbon) moiety. Unless otherwise specified, the hydrocarbon moiety can represent a saturated or unsaturated, and straight-chained, branched, or cyclic hydrocarbon group containing at least one carbon atom. In different embodiments, the hydrocarbon moiety can preferably possess, for example, one, two, three, four, five, six, seven, or eight carbon atoms, or a minimum number of carbon atoms corresponding to any one of the foregoing examples of carbon atoms, or a range of carbon atoms resulting from any two of the foregoing examples of carbon atoms.

The surfactants typically associate with the particle surface by forming an interface between the particle surface and the aqueous solution. In order to function as a surfactant, the surfactant is used in a concentration high enough for surfactant molecules to associate with surfaces of the particles to an extent that precipitation of the particles is facilitated. Such a surfactant concentration is herein also referred to as an "effective concentration" of surfactant. Preferably, an effective concentration of surfactant is one that also permits size control or shape control of the particles during growth of the particles. Generally, the surfactant concentration is at least 100 mg/L (i.e., 0.01 wt % or 100 ppm). In different embodiments, the surfactant concentration can preferably be at, greater than, or less than 100, 200, 300, 400, 500, 600, 700, 800, 900, or 1,000 mg/L, or a range of concentrations resulting from any two of the foregoing exemplary values.

In a first embodiment, the surfactant component includes one or more organosiloxane (i.e., organosilicone) molecules and/or polymers. The organosiloxane molecule or polymer contains a hydrocarbon moiety and at least one Si—OH or Si—OR moiety, wherein the R group and hydrocarbon moiety independently represent any of the types of hydrocarbon moieties described above.

The organosiloxane can be, for example, a monosiloxane (i.e., contains one Si atom). The monosiloxane can, in turn, be a monoalkoxysilane, dialkoxysilane, or trialkoxysilane. Some examples of monoalkoxysilanes include trimethylmethoxysilane, trimethylethoxysilane, triethylmethoxysilane, tri-(n-propyl)methoxysilane, tri-(n-butyl)methoxysilane, tri-(isobutyl)methoxysilane, tri-(n-pentyl) methoxysilane, tri-(n-hexyl)methoxysilane, dimethylethylmethoxysilane, n-propyldimethylmethoxysilane, and vinyldimethylmethoxysilane. Some examples of dialkoxysilanes include dimethyldimethoxysilane, dimethyldiethoxysilane, diethyldimethoxysilane, di-(n-propyl)dimethoxysilane, di-(n-butyl)dimethoxysilane, di-(isobutyl)dimethoxysilane, di-(n-pentyl)dimethoxysilane, di-(n-hexyl)dimethoxysilane, methylethyldimethoxysilane, and n-propylmethyldimethoxysilane). Some examples of trialkoxysilanes include methyltrimethoxysilane, methyltriethoxysilane, etyltrimethoxysilane, n-propyltrimethoxysilane, n-butyltrimethoxysilane, isobutyltrimethoxysilane, n-pentyltrimethoxysilane, isopentyltrimethoxysilane, n-hexyltrimethoxysilane, n-heptyltrimethoxysilane, n-octyltrimethoxysilane, n-nonyltrimethoxysilane, n-decyltrimethoxysilane, 2-hydroxyethyltrimethoxysilane, and 3-hydroxypropyltrimethoxysilane. The corresponding monohydroxysilanes, dihydroxysilanes, or trihydroxysilanes (i.e., wherein the alkoxy group is substituted by a hydroxy group) are also considered herein as suitable examples.

The organosiloxane can also be, for example, a disiloxane (i.e., contains two Si atoms). Some examples of suitable disiloxane molecules include hexamethyldisiloxane, hexaethyldisiloxane, and hexaphenyldisiloxane. The disiloxane may also be incompletely substituted with hydrocarbon groups such that silylhydride (Si—H) groups are present. Some examples of such disiloxane molecules include pentamethyldisiloxane, 1,1,3,3-tetramethyldisiloxane, and 1,1,3,3-tetraethyldisiloxane. Disiloxane groups in which the hydrocarbon groups are replaced by alkoxy or hydroxy groups are also considered herein.

The organosiloxane can also be, for example, a trisiloxane (i.e., contains three Si atoms). Some examples of suitable trisiloxane molecules include octamethyltrisiloxane, octaethyltrisiloxane, and 1,1,1,5,5,5-hexamethyl-3,3-diphenyltrisiloxane. The trisiloxane may also be incompletely substituted with hydrocarbon groups such that silylhydride groups are present. Some examples of such trisiloxane molecules include heptamethyltrisiloxane (commercially available, e.g., Drift® Snowmaking Additive, Aquatrols, 1273 Imperial Way, Paulsboro, N.J. 08066), 1,1,1,5,5,5-hexamethyltrisiloxane, and 1,1,3,3,5,5-hexamethyltrisiloxane. Trisiloxane groups in which the hydrocarbon groups are replaced by alkoxy or hydroxy groups are also considered herein.

Other suitable organosiloxane molecules include, for example, the tetrasiloxanes, pentasiloxanes, hexasiloxanes, polysiloxanes, cyclotrisiloxanes, cyclotetrasiloxanes, cyclopentasiloxanes, cyclohexasiloxanes, silsesquioxanes, and their silylhydride-, alkoxy-, and hydroxy-containing forms. The organosiloxanes may also be substituted with any suitable functional groups, e.g., one or more epoxy, glycidyl, ethyleneoxide, di(ethyleneoxide), poly(ethyleneoxide), amide, keto, ether, fluoro, ebloro, or carboxylic acid groups.

In a second embodiment, the surfactant component includes one or more ammonium salt molecules and/or polymers. The ammonium molecule or polymer contains a hydrocarbon moiety as described above and at least one positively charged amino group (e.g., at least one $NR_4^+$ group in the case of a quaternary ammonium group, wherein the four R groups are each independently a hydrocarbon moiety as described above). Preferably, the hydrocarbon moiety is composed only of carbon and hydrogen, and optionally, fluorine atoms. Fluorine atoms, if present, may substitute a portion of or all of the hydrogen atoms of the hydrocarbon moiety. The counteranion of the ammonium salt is not particularly limited, and can be, for example, a halide, nitrate, sulfate, triflate, oxalate, carbonate, bicarbonate, or acetate. Some examples of suitable ammonium groups include trimethylammonium, tetramethylammonium, tetraethylammonium, tetrapropylammonium, tetrabutylammonium, dimethyldibutylammonium, tetraphenylammonium, trimethylbenzylammonium, n-butyltrimethylammonium, n-pentyltrimethylammonmum, n-hexyltrimethylammonium, n-heptyltrimethylammonium, n-octyltrimethylammonium, n-nonyltrimethylammonium, and n-decyltrimethylammonium. Other ammonium groups include ring ammonium groups (e.g., pyridinium, piperidinium, pyrazinium, piperazinium, and imidazolium), wherein the ring can be substituted by one or more hydrocarbon groups. A particular ammonium-containing surfactant suitable for use herein is a mixture of one or more quaternary ammonium compounds with one or more tertiary amines. An example of such a mixture can be found under the trade name Armoclear 2550, supplied by Akzo Nobel Surface Chemistry, Stenungsund, Sweden.

In a third embodiment, the surfactant component includes one or more carboxylic acid molecules and/or polymers. The carboxylic acid molecule or polymer contains a hydrocarbon moiety (as described above) and at least one carboxylic acid group. Preferably, the hydrocarbon moiety is composed only of carbon and hydrogen, and optionally, fluorine atoms. Fluorine atoms, if present, may substitute a portion or all of the hydrogen atoms of the hydrocarbon moiety. As used herein, "carboxylic acid" also includes the corresponding carboxylic acid salt (i.e., "carboxylate"), and vice-versa. The carboxylate can include any suitable counteranion, as described above. The carboxylic acid molecule can be, for example, a monocarboxylic acid, dicarboxylic acid, or tricarboxylic acid. Some examples of suitable carboxylic acid molecules include acetate, propionate, butyrate, valerate (pentanoate), hexanoate, heptanoate, octanoate, decanoate, undecanoate, laurate, myristate, palmitate, benzoate, oxalate, malonate, fumarate, maleate, succinate, glutarate, phthalate, citrate, and trifluoroacetate. In one embodiment, as exemplified above, the hydrocarbon moiety of the carboxylic acid molecule is unsubstituted, i.e., contains only carbon and hydrogen. In another embodiment, the hydrocarbon moiety is substituted with one or more ether, amido, keto, amino (primary, secondary, or tertiary), fluoro, or chloro groups Some examples of amino-substituted carboxylic acid molecules include glycine, alanine, 3-aminopropanoic acid, 4-aminobutyric acid, 6-aminohexanoic acid, 11-aminioundecanoic acid, and p-aminobenzoic acid.

In a fourth embodiment, the surfactant component includes one or more alcohol molecules and/or polymers. The alcohol molecule or polymer contains a hydrocarbon moiety (as described above) and at least one alcohol (OH) group. Preferably, the hydrocarbon moiety is composed only of carbon and hydrogen, and optionally, fluorine atoms. Fluorine atoms, if present, may substitute a portion or all of the hydrogen atoms of the hydrocarbon moiety. The alcohol can be, for example, a mono-alcohol, diol, triol, or polyol. Some examples of suitable alcohols include methanol, ethanol, n-propanol, isopropanol, n-butanol, isobutanol, t-butanol, sec-butanol, n-pentanol (amyl alcohol), isopentanol (isoamyl alcohol), neopentanol, n-hexanol, phenol, benzyl alcohol, ethylene glycol, propylene glycol, 1,3-propanediol, 1,4-butanediol, 2,3-butanediol, 1,5-pentanediol, trifluoromethanol, 4-fluorophenol, pentafluorophenol, and polyvinylalcohol (PVA). Preferably, the alcohol contains at least four, five, or six carbon atoms. The alcohol is preferably straight-chained.

In a fifth embodiment, the surfactant component includes one or more metal diketones. The metal portion of the metal diketone can be any charged metal ion capable of forming a complex with a diketone molecule. Preferably, the metal is a transition metal, and more preferably, a first-row transition metal. Even more preferably, the metal is Fe(III), which corresponds to the class of iron (III) diketones. The diketone portion can be any diketone molecule capable of forming a complex with a metal ion. Preferably, the diketone is in the form of a diketonate, which refers to a negatively charged diketone molecule wherein a proton has been removed (i.e., conjugate base of the diketone). Some examples of diketone molecules include 2,3-butanedione, 2,4-pentanedione (acetylacetone), and 2,5-hexanedione. Of particular focus herein are the metal acetylacetonates (i.e., "metal acace" or "metal ACAC" complexes). Some examples of metal acac complexes include $V(III)(acac)_3$, $V(IV)(O)(acac)_2$, $Cr(III)(acac)_3$, $Mn(III)(acac)_3$, $Fe(III)(acac)_3$, $Co(II)(acac)_2$, $Ni(II)(acac)_2$, $Cu(II)(acac)_2$, $Zn(II)(acac)_2$, $Ru(III)(acac)_3$, $Pd(II)(acac)_2$, $Cd(II)(acac)_2$, and $Al(III)(acac)_3$. In a preferred embodiment, the metal diketonate is $Fe(III)(acac)_3$.

In a sixth embodiment, the surfactant component includes one or more fluorohydrocarbon compounds or polymers. The fluorohydrocarbon compounds can be saturated or unsaturated, and straight-chained, branched, or cyclic. Preferably, the fluorohydrocarbon compounds contain at least four, five, six, seven, or eight carbon atoms. In one embodiment, the fluorohydrocarbon compounds are completely substituted with fluoro groups such that the compounds are composed of only carbon and fluorine atoms (i.e., the "perfluoro" compounds). In another embodiment, the fluorohydrocarbon compounds are incompletely substituted with fluoro groups such that the compounds are composed of carbon, hydrogen, and fluorine atoms. Some examples of suitable fluorohydrocarbon compounds include perfluoropentane, perfluorohexane, perfluoroheptane, perfluorooctane, perfluorodecalin, perfluoromethylcyclobutane (empirical formula $C_5F_{10}$), perfluorodimethylcyclobutane (empirical formula $C_6F_{12}$), perfluoromethylcyclopentane, (trifluoromethyl)cyclopentane, his-1,3-(trifluoromethyl)cyclopentane, perfluorodimethylcyclopentane (1,2- or 1,3-dimethyl isomers, or a mixture thereof), perfluoromethylcyclohexane, perfluorodimethylcyclohexane (1,2-, 1,3-, or 1,4-dimethyl isomers, or a mixture thereof), bis-1,4-(trifluoromethyl)cyclohexane, perfluoroethylcyclohexane, perfluoroisopropylcyclohexane, perfluorotrimethylcyclohexane, perfluorocycloheptane, perfluorocyclooctane, octafluoronaphthalene, perfluorotoluene, and perfluoroxylenes.

In a seventh embodiment, the surfactant component includes one or more bacterial proteins. Some particular bacterial proteins considered herein are ice-nucleating proteins derived from *Pseudomonas syringae*. These proteins are commercially available, e.g., under the trade name Snomax®.

The five reaction components described above (i.e., metal-reducing microbes, culture medium, surfactant, reducible metal oxide component, and electron donor) are combined in a suitable container and subjected to conditions (e.g., temperature and reaction time) suitable for producing the nanoparticles from the reaction components. In one embodiment, the container for holding the reaction components is simple by containing no more than container walls, a bottom, and a lid. In another embodiment, the container is more complex by including additional features, such as inlet and outlet elements for gases, liquids, or solids, one or more heating elements, nanoparticle separation features (e.g., traps or magnets), one or more agitating elements, fluid recirculating elements, electronic controls for controlling one or more of these or other conditions, and so on.

The components may be combined in any suitable manner. For example, each of the five reaction components or a combination thereof (e.g., the metal-reducing microbes and cell culture) may be prepared before the components are combined, or alternatively, obtained in a pre-packaged form before the components are combined. When components or combinations thereof are provided in package form, the packaged forms may be designed to be used in their entireties, or alternatively, designed such that a portion of each is used (e.g., as aliquots of a concentrate).

In one embodiment, the reaction components are combined immediately before the reaction components are subjected to suitable reaction conditions for producing metal oxide nanoparticles. This embodiment is particularly useful for the case when the reaction components react on contact with each other (i.e., upon being combined) to produce nanoparticles.

In another embodiment, at least two of the reaction components are substantially unreactive with each other such that they can be in a combined state for a substantial period of time before use without significant degradation or production of nanoparticles. The substantial period of time is preferably a conventional time of storage (e.g., at least one week, one month, three months, six months, or a year). This embodiment can be beneficial by simplifying the process, specifically, by lessening the number of addition steps (i.e., less than five). In a particular embodiment, a solution containing at least three or four of the components is storage-stable under specified conditions (e.g., reduced temperature). Production of nanoparticles can begin when the remaining one or two components are added, and after the combination is subjected to conditions conducive to microbial-mediated formation of metal oxide nanoparticles. Alternatively, a solution containing all of the components is storage-stable. When production of nanoparticles is desired, the solution is subjected to conditions conducive to microbial-mediated formation of metal oxide nanoparticles. In addition, storage-stable samples of the reaction components can be provided in the form of a kit. The samples in the kit can contain individual or combined reaction components.

The method is practiced by subjecting the combined components to conditions that induce the formation of metal oxide nanoparticles therefrom. Some of the conditions that can affect formation of metal oxide nanoparticles from the combined components include temperature, reaction time, precursor metal concentration, pH, and type of microbes used. In some embodiments, the reaction conditions may not require any special measures other than combining the reaction components at room temperature (e.g., 15-25° C.) and waiting for nianoparticles to grow over a period of time. In other embodiments, the combined reaction components are either heated, cooled, or modified in pH, in order to induce nanoparticle formation.

When thermophilic microbes are used, the temperature at which the reaction is conducted can preferably be at least, for example, 40° C., 45° C., 50° C., 55° C., 60° C., 65° C., 70° C., 75° C., 80° C., 85° C., or 90° C. depending on the type of thermophilic microbes being used. Any range resulting from any two of the foregoing values is also contemplated herein. When mesophilic microbes are used, the temperature can preferably be at least 15° C., 20° C., 25° C., or 30° C., and up to any of the temperatures given above for thermophilic microbes. When psychrophilic microbes are used, the temperature at which the reaction is conducted can preferably be less than, for example, 40° C., or at or less than 35° C., 30° C., 25° C., 20° C., 15° C., 10° C., 5° C., 0° C., or −5° C., or any range resulting from any two of the foregoing values. It is to be appreciated that, even though different exemplary temperatures have been given for each type of microbe, each type of microbe may be capable of thriving in temperatures well outside the typical temperatures given above. For example, a thermophilic microbe may also be capable of thriving to a useful extent at temperatures below 40° C. where mesophilic microbes traditionally thrive; or mesophilic or thermophilic microbes may be capable of thriving to a useful extent at temperatures below 15° C. (i.e., by being psychrotolerant in addition to mesophilic or thermophilic). Particularly when employing *Thermoanaerobacter* sp. strain TOR-39, the temperature is preferably maintained between about 45° C. and 75° C.

The reaction (incubation) time is the period of time that the combined reaction components are subjected to reaction conditions necessary for producing nanoparticles. The reaction time is very much dependent on the other conditions used, as well as the characteristics desired in the nanoparticle product. For example, shorter reaction times (e.g., 1-60 minutes) may be used at elevated temperature conditions whereas longer reaction times (e.g., 1-7 days, or 1-3 weeks) may be used at lower temperatures to obtain a similar yield of product. Typically, shorter reaction times produce smaller particles than particles produced using longer reaction times under the same conditions. The incubation may be, for example, between 3 and 30 days, depending on the amount and size of the crystalline nanoparticle product desired.

The pH can also be suitably adjusted. Generally, when using thermophilic bacteria, the pH value is preferably within the range of 6.5-9. For example, particularly when employing *Thermoanaerobacter* sp. strain TOR-39, the pH is preferably maintained at a level between about 6.9 and 7.5. In different embodiments, depending on the microbe and other conditions, the pH is preferably acidic by being less than 7 (e.g., a pH of or less than 6.5, 6.0, 5.5, 5.0, 4.5, 4.0, 3.5, 3.0, 2.5, 2.0, 1.5, 1.0, or a range resulting from any two of these values), or preferably alkaline by being above 7 (e.g., a pH of or greater than 7.5, 8.0, 8.5, 9.0, 9.5, 10, 10.5, 11, 11.5, or a range resulting from any two of these values), or preferably approximately neutral by having a pH of about 7, e.g., 6.5-7.5.

In addition to selecting reaction conditions (e.g., temperature, reaction time, and pH) on the basis of permitting or inducing the formation of nanoparticles, the reaction conditions can also be selected for numerous other purposes, including to modify or optimize the product yield, production efficiency, particle size or size range, particle composition or phase (e.g., crystalline vs. semicrystalline vs. amorphous), or particle morphology. For example, lower reaction temperatures may be employed to provide a more pure or single-crystalline product.

Once the nanoparticles are produced, they are isolated (i.e., separated) from the reaction components and byproducts formed by the reaction products. Any method known in the art for separation of nanoparticles from reaction components can be used herein.

In one embodiment, nanoparticles are separated from the reaction components by allowing the nanoparticles to settle to the bottom of the container and then decanting the liquid medium or filtering off the nanoparticle product. The collected crystalline nanoparticle product may be washed one or more times to further purify the product. The reaction container may optionally be fitted with a drain valve to allow the solid product to be removed without decanting the medium or breaking gas seals.

In another embodiment, the container in which the reaction components are housed is attached to (or includes) an external trap from which the crystalline nanoparticle product can be removed. The trap is preferably in the form of a recess situated below flowing reaction solution. Nanoparticles in the flowing reaction solution are denser than the reaction solution, and hence, will settle down into the trap. The flowing reaction solution is preferably recirculated.

In another embodiment, a filter is used to trap the nanoparticles. The filter can be in the form of multiple filters that trap successively smaller particles. Depending on the particle size and other variables, the one or more filters that trap the nanoparticles may contain a pore size of no more than about 0.5, 0.4, 0.3, 0.25, 0.2, 0.1, or 0.05 μm.

In yet another embodiment, in the case where the nanoparticle product is magnetic, a magnetic source (e.g., electromagnet or other suitable magnetic field-producing device) can be employed to collect the nanoparticles. The magnetic source can be used as the sole means of separation, or used in combination with other separation means, such as a trap or filter.

The method of the invention can be performed in a batchwise manner or in a continuous manner. Examples of suitable arrangements for performing the method of the invention in a continuous manner are described in U.S. Pat. No. 6,444,453, particularly FIGS. 3 and 4 therein, all of which is incorporated by reference herein. In addition to the size control afforded by the surfactant, continuous collection of nanoparticle product from a recirculating fluid may also be used as a further means of controlling particle size, because the particles tend to grow larger the longer they remain in the culture. In addition to the effect of the surfactant on shedding nanoparticles from the microbes, the degree of fluid circulation (e.g., flow rate) can further promote shedding of the nanoparticles from the microbes.

The metal oxide nanoparticles produced by the method can have any of the types of metal oxide compositions known in the art in which at least one metal is not in a highest oxidized state. Some examples of nanoparticle metal oxide compositions include $Cr_2O_3$, FeO, MnO, $Mn_2O_3$, $MnO_2$, $MnO_3$, CoO, NiO, $Cu_2O$, NbO, $NbO_2$, SnO, $MoD_2$, $WO_2$, paratungstates, polyoxometallates (e.g., polyoxomolybdates, polyoxotungstates, and polyoxovanadates), and combinations thereof.

In a preferred embodiment, the nanoparticles produced by the method have a spinel oxide composition according to the general formula:

$$M_x'M''_{3-x}O_4 \qquad (1)$$

In formula (1) above, M' and M" are the same or different metal cations. Typically, at least one of M' and M" is a transition metal cation, and more typically, a first-row transition metal cation. In order to maintain charge neutrality with the four oxide atoms, the oxidation states of M' and M" sum to +8. Generally, two-thirds of the metal ions are in the +3 state while one-third of the metal ions are in the +2 state. The +3 metal ions generally occupy an equal number of tetrahedral and octahedral sites, whereas the +2 metal ions generally occupy half of the octahedral sites. However, formula (1) includes other chemically-acceptable possibilities, including that the +3 metal ions or +2 metal ions occupy only octahedral or tetrahedral sites, or occupy one type of site more than another type of site. The subscript x can be any numerical (integral or non-integral) positive value, typically at least 0.01 and up to 1.5.

When a single metal is used in the precursor composition, then M' and M" in formula (1) are the same and formula (1) becomes simplified to the general formula:

$$M_3O_4 \qquad (2)$$

Some examples of nanoparticle compositions according to formula (2) include $Fe_3O_4$ (magnetite), $Co_3O_4$, and $Mn_3O_4$.

When two reducible metals are used in the precursor composition (e.g., $Fe^{3+}$ and $Co^{3+}$), either one (or both) of the metal ions are in a reduced oxidation state in the resulting nanoparticle composition. Some examples of classes of spinel oxide nanoparticle compositions having two metals include those of the general composition $M'_yFe_{3-y}O_4$ (e.g., $Ti_yFe_{3-y}O_4$, $V_yFe_{3-y}O_4$, $Cr_yFe_{3-y}O_4$, $Mn_yFe_{3-y}O_4$, $Co_yFe_{3-y}O_4$, $Ni_yFe_{3-y}O_4$, $Cu_yFe_{3-y}O_4$, $Zn_yFe_{3-y}O_4$, $Pd_yFe_{3-y}O_4$, $Pt_yFe_{3-y}O_4$, $Cd_yFe_{3-y}O_4$, $Ru_yFe_{3-y}O_4$, $Zr_yFe_{3-y}O_4$, $Nb_yFe_{3-y}O_4$, $Gd_yFe_{3-y}O_4$, $Eu_yFe_{3-y}O_4$, $Tb_yFe_{3-y}O_4$, and $Ce_yFe_{3-y}O_4$); the general composition $M'_yCo_{3-y}O_4$ (e.g., $Ti_yCo_{3-y}O_4$, $V_yCO_{3-y}O_4$, $Cr_yCo_{3-y}O_4$, $Mn_yCo_{3-y}O_4$, $Ni_yCO_{3-y}O_4$, $Cu_yCO_{3-y}O_4$, $Zn_yCo_{3-y}O_4$, $Pd_yCo_{3-y}O_4$, $Pt_yCO_{3-y}O_4$, $Cd_yCO_{3-y}O_4$, $Ru_yCo_{3-y}O_4$, $Zr_yCo_{3-y}O_4$, $Nb_yCo_{3-y}O_4$, $Gd_yCo_{3-y}O_4$, $Eu_yCo_{3-y}O_4$, $Tb_yCo_{3-y}O_4$, and $Ce_yCo_{3-y}O_4$); and the general composition $M'_yNi_{3-y}O_4$ (e.g., $Ti_yNi_{3-y}O_4$, $V_yNi_{3-y}O_4$, $Cr_yNi_{3-y}O_4$, $Mn_yNi_{3-y}O_4$, $Fe_yNi_{3-y}O_4$, $Cu_yNi_{3-y}O_4$, $Zn_yNi_{3-y}O_4$, $Pd_yNi_{3-y}O_4$, $Pt_yNi_{3-y}O_4$, $Cd_yNi_{3-y}O_4$, $Ru_yNi_{3-y}O_4$, $Zr_yNi_{3-y}O_4$, $Nb_yNi_{3-y}O_4$, $Gd_yNi_{3-y}O_4$, $Eu_yNi_{3-y}O_4$, $Tb_yNi_{3-y}O_4$, and $Ce_yNi_{3-y}O_4$), wherein y in the general compositions given above represents an integral or non-integral numerical value of at least 0.1 and up to 2; and M' represents one or a combination of metal ions, e.g., $(M'_a,M''_b)_yFe_{3-y}O_4$, wherein subscripts a and b are non-integral numbers that sum to 1 (e.g., $Mn_{0.5}Zn_{0.5}Fe_2O_4$, $Mn_{0.4}Zn_{0.6}Fe_2O_4$, $Ni_{0.5}Co_{0.5}Fe_2O_4$, and $Ni_{0.4}Co_{0.6}Fe_2O_4$).

The resulting particles have nanoscale dimensions (i.e., are nanoparticles). By having nanoscale dimensions, at least one dimension of the nanoparticles is below 1 micron (1 µm). In different embodiments, the nanoparticles can have at least one dimension of at least 1 nm, 2 nm, 5 nm, 10 nm, 20 nm, 30 nm, 40 nm, 50 nm, 100 nm, 200 nm, 300 nm, 400 nm, or 500 nm, or any range therebetween, or between any of the foregoing values and 1 µm. In a particular embodiment, all of the dimensions of the nanoparticles are in the nanoscale realm.

The nanoparticles can be adjusted in their nanoparticle size (or range thereof) by, inter alia, choice of surfactant and the amount of surfactant used. Generally, higher surfactant concentrations promote formation of smaller particle sizes while lower surfactant concentrations promote formation of larger particle sizes. For example, a surfactant (and amount thereof can be selected such that at least 80%, 85%, 90%, 95%, or 98% of the nanoparticles are within a size range spanning about 500 nm (e.g., 10-500 nm), 400 nm, 300 nm, 200 nm, 100 nm, 50 nm, 20 nm (e.g., 30-50 nm), or 10 nm (e.g., 30-40 nm).

The resulting nanoparticles can also have any suitable morphology (shape). Some examples of possible nanoparticle shapes include amorphous, fibrous, tubular, cylindrical, spherical, ovoidal, pyramidal, cuboidal, rectangular, dodecahedral, octahedral, and tetrahedral. The nanoparticles can be adjusted in their shape by, inter alia, choice of surfactant and the amount of surfactant used. This phenomenon can be attributed to the fact that some surfactants exhibit differences in their tendency to adsorb onto different crystallographic planes (or faces) of a crystal (a process sometimes referred to as "poisoning" of the surface). When particular crystallographic surfaces are poisoned by surface-active species, the growth rate in the direction normal to those surfaces will be slower than growth in other directions, thereby leading to the development of crystallites that are not equiaxed but instead may become rods, needles, laths, or platelets. For example, the metal oxide nanoparticles produced according to the methods of the present invention may be equiaxed euhedral crystals (typically cubes, octahedra, and modifications thereof as are typical of spinel-type oxides).

Referring to FIG. 1, a process diagram for forming a selected metal oxide is provided. A hydrous metal oxide feedstock is provided, preferably as a dispersed colloidal solid particulate, at least one metal of which is capable of being reduced from a higher to a lower oxidation state. The feedstock may contain a single reducible metal (e.g., Fe(III)), more than one reducible metal (e.g., Fe(III) and Co(III) or Fe(III) and Cr(VI)) or a reducible metal and a non-reducible metal (e.g., Fe(III) and Zn(II)). Cultures are established using bacteria suitable for reducing the metal oxide precursor in the presence of an electron donor. The electron donor supports the metabolism of the bacteria that culminates with reduction of the hydrous metal oxide to a second product phase.

The method may include one or more chemicals that can facilitate reduction of one or more precursor metal ions. However, the production of nanoparticles remains microbially-mediated.

Preferably, conditions are avoided in which metal ions are chemically (i.e., directly) reduced without microbial mediation. Some of the conditions that can affect whether metal ions are directly or microbially reduced include the presence or absence of a chemical reductant, the choice of chemical reductant, the processing temperature, and the choice of microbes. For example, if a chemical reductant is predominantly consumed by the microbes and used in a microbial-mediated process for reducing one or more metal ions, then the presence of the chemical reductant does not obviate the goals of the method. However, the method described herein preferably excludes the use of stronger reductants in the method because such reductants may have the ability to directly reduce one or more metal ions before microbial consumption of the reductant, if possible, can take place. As used herein, a "stronger reductant" is meant to be a chemical stronger in reducing power than the known weaker reductants, such as citrate, reducing sugars, alcohols, and hydrogen gas, under standard conditions. Some examples of chemical reductants preferably excluded from use in the method include the hydrides (e.g., borohydrides and aluminum hydrides), hydrazines, hypophosphorous acid, and Sn(II) metal salts. It is understood that weaker reductants, such as the exemplary ones given, may also be unsuitable for the method described herein if conditions are provided that render these reductants capable of directly reducing metal ions (e.g., by use of temperatures high enough to cause direct reduction as the main reductive process).

Examples have been set forth below for the purpose of illustration and to describe certain specific embodiments of the invention. However, the scope of this invention is not to be in any way limited by the examples set forth herein.

EXAMPLE 1

Preparation of Fe(III) Oxyhydroxide (FeOOH) Precursor Composition

Fe(III) oxyhydroxide as magnetite precursor was prepared as follows: NaOH solution (10 M) was added dropwise into a solution of 0.4 M of $FeCl_3.6H_2O$ with rapid stirring, and then stopped when the solution reached a pH of about 7.00. The suspension was aerated overnight by magnetic stirring, ensuring homogeneous oxidation of the precursors. The formed Fe(III) phases were washed five times in deionized water and centrifuged after each washing. A final solution of about 0.4 M FeOOH was flushed with $N_2$ and stored under $N_2$ headspace for one month.

The culture medium had the same composition to Roh et al., *Solid State Commun.* 118: 529-534 (2001) supplemented with trace minerals and vitamin solutions (see Phelps et al., *Geomicrobiol. J.,* 7: 79-91 (1989)). The dissolved basal medium was boiled with $N_2$ purging and cooled with continuous $N_2$ purging. For serum vial tests, 50 mL aliquots were dispensed into 160 mL serum bottles with $N_2$ purging and had a final pH of about 8.0-8.2. Each bottle was sealed with a butyl rubber stopper (Bellco Glass, Inc.) and an aluminum crimp seal. The incubation for controlled microbial synthesis of magnetites in duplicates was initiated with the addition of 20 mM of glucose, 16 mM of precursor and 0.2 mL of mid-log growth of metal reducing culture of TOR-39, some aliquot (i.e., within an effective concentration, as described above) of size control agent stock solution at 5 to 1,000 mg/l concentration levels and 15 mM of MOPS buffer (pH 7.8), if desired. The incubation was at 65° C. for 30 days for TOR-39. Control samples receiving an equal volume of pure akaganeite were also incubated.

EXAMPLE 2

Relationship Between Surfactant Concentration and Nanoparticle Characteristics

In a series of experiments, cultures of *T. ethanoticus* strain TOR-39 as generally taught in U.S. Pat. No. 6,444,453 were established. The following surfactants were examined: modified heptamethyltrisiloxane (Drift® Snowmaking Additive, Aquatrols, 1273 Imperial Way, Paulsboro, N.J. 08066); trifluoroacetic acid (i.e., "TFA" or "$CF_3COOH$"); a mixture of quaternary ammonium compounds and tertiary amines (Armoclear 2550, Akzo Nobel Surface Chemistry, Stenungsund, Sweden); iron acetylacetonate (Fe-acac); p-aininobenzoic acid (BA); perfluoromethylcyclopentane (PMCP); decanoic acid (DA); ethanol; methanol; and a bacterial protein (Snomax® Snow Inducer, York Snow, Inc., 7257 S. Revere Pkwy., Centennial, Colo. 80112).

A first set of screening experiments were carried out using 50 mL batches of *Thermoanaerobacter* sp. TOR-39, cultured as taught in U.S. Pat. No. 6,444,453 by using 20 mM glucose and 16 mM FeOOH. Each surfactant was added in the form of a dilute stock solution to avoid localized toxicity to the bacteria. As noted, most batches yielded relatively phase-pure magnetite, but a few yielded mixed magnetite-akaganeite. The following table summarizes the results. When replicate batches were run, the average size for the two replicates is also shown.

TABLE 1

Effect of Surfactant on Nanoparticle Product

| Surfactant | Conc., ppm | Yield, mg | Ave yield, mg | Phase | Size, nm | Ave. size, nm |
|---|---|---|---|---|---|---|
| DRIFT | 5 | 43 | | mixed | — | |
| DRIFT | 5 | 64 | | magnetite | 33 | |
| DRIFT | 25 | 47 | 51.3 | mixed | — | |
| AA | 5 | 63 | | magnetite | 40 | |
| AA | 5 | 58 | | magnetite | 37 | 38.5 |
| AA | 25 | 61 | 60.7 | magnetite | 29 | 29 |
| Snomax | 5 | 65 | | magnetite | 29 | |
| Snomax | 5 | 55 | | magnetite | 29 | 29 |
| Snomax | 25 | 65 | 61.7 | magnetite | 25 | 25 |
| MeOH | 5 | 60 | | magnetite | 28 | |
| MeOH | 5 | 54 | | magnetite | 25 | 26.5 |
| MeOH | 25 | 57 | 57 | magnetite | 30 | 30 |
| PMCP | 5 | 56 | | magnetite | 22 | |
| PMCP | 5 | 59 | | magnetite | 32 | 27 |
| PMCP | 25 | 54 | 56.3 | magnetite | 20 | 20 |
| FeACAC | 20 | 58 | | magnetite | 19 | |
| FeACAC | 20 | 58 | | magnetite | 22 | 20.5 |
| FeACAC | 200 | 56 | 56.7 | magnetite | 20 | 20 |
| DA | 20 | 57 | | magnetite | 22 | |
| DA | 20 | 59 | | magnetite | 26 | 24 |
| DA | 140 | 60 | 58.7 | magnetite | 25 | 25 |
| BA | 20 | 59 | | magnetite | 22 | |
| BA | 20 | 59 | | magnetite | 25 | 23.5 |
| BA | 100 | 61 | 59.7 | magnetite | 24 | 24 |
| TFA | 20 | 66 | | magnetite | 15 | |
| TFA | 20 | 66 | | magnetite | 28 | 21.5 |
| TFA | 80 | 66 | 66 | magnetite | 26 | 26 |
| control | | 60 | | magnetite | 20 | |
| control | | 67 | | magnetite | 30 | 25 |
| control | | 57 | | magnetite | 25 | 25 |

Figure 2:
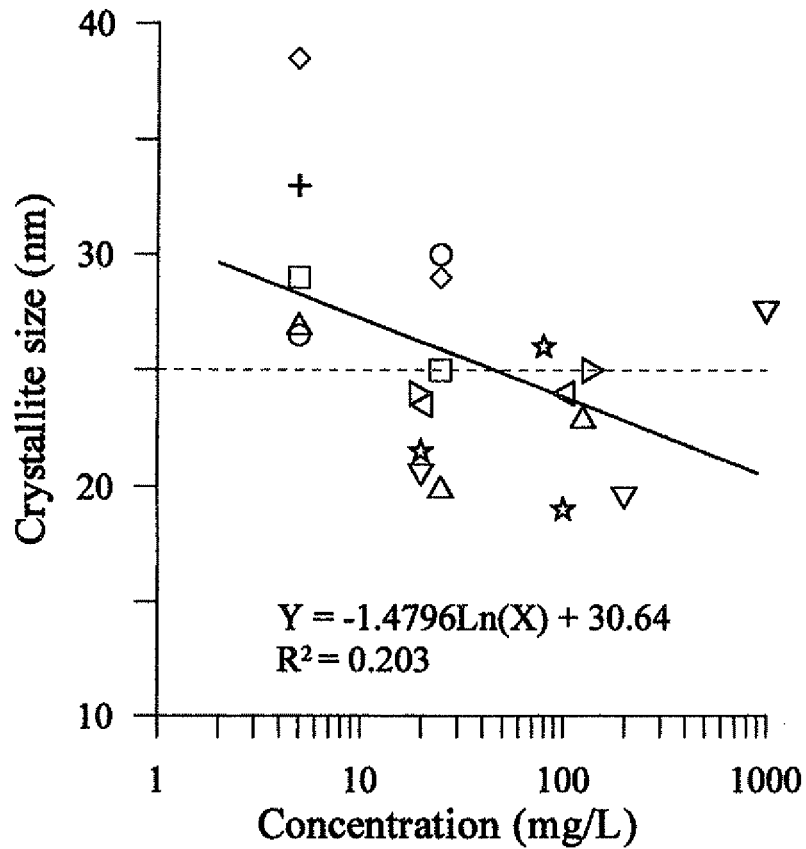
FIG. 2. A graph showing a generally inverse relationship between surfactant concentration and crystallite size for nine surfactants, with data from a control batch shown for comparison.

The results in the above table are presented graphically in FIG. 2, where it can be seen that there is a generally inverse relationship between surfactant concentration and particle size. The scatter in the data suggests that some surfactants are more effective than others for this combination of bacterial strain and metal oxide (pure iron oxide). The results clearly show that the addition of these particular surfactants can be tolerated by the bacteria and be usefully employed to modify the size of particulates produced in the fermentative process.

EXAMPLE 3

Relationship Between Higher Surfactant Concentration and Nanoparticle Size

A second set of experiments with similar culture conditions to the previous example were carried out using higher surfactant concentrations as summarized in the following table.

TABLE 2

Effect of Higher Surfactant Concentration on Nanoparticle Product

| Surfactant | Conc., ppm | Incubation period, mo. | Phase | Size, nm |
|---|---|---|---|---|
| PMCP | 25 | 1 | magnetite | |
| PMCP | 25 | 1 | magnetite | 20 |
| PMCP | 25 | 2 | magnetite | |
| PMCP | 25 | 2 | magnetite | 16 |
| PMCP | 125 | 1 | magnetite | 21 |
| PMCP | 125 | 1 | magnetite | 25 |
| FeACAC | 200 | 1 | magnetite | |
| FeACAC | 200 | 1 | magnetite | 19 |
| FeACAC | 200 | 2 | magnetite | 20 |
| FeACAC | 200 | 2 | magnetite | 23 |
| FeACAC | 1000 | 1 | magnetite | 22 |
| FeACAC | 1000 | 1 | magnetite | 33 |
| FeACAC | 1000 | 2 | magnetite | 23 |
| FeACAC | 1000 | 2 | magnetite | 22 |
| DA | 200 | 2 | magnetite | |
| DA | 200 | 2 | magnetite | |
| DA | 1000 | 1 | magnetite | |
| DA | 1000 | 1 | magnetite | |
| DA | 1000 | 2 | magnetite | |
| DA | 1000 | 2 | magnetite | |
| BA | 100 | 1 | magnetite | 21 |
| BA | 100 | 1 | magnetite | |
| BA | 100 | 2 | magnetite | |
| BA | 100 | 2 | magnetite | |
| BA | 500 | 1 | magnetite | |
| BA | 500 | 1 | magnetite | |
| BA | 500 | 2 | magnetite | |
| BA | 500 | 2 | magnetite | 16 |
| TFA | 100 | 1 | magnetite | 20 |
| TFA | 100 | 1 | magnetite | 18 |
| TFA | 100 | 2 | magnetite | 28 |
| TFA | 100 | 2 | magnetite | 43 |
| TFA | 1000 | 1 | magnetite | |
| TFA | 1000 | 1 | magnetite | |
| TFA | 1000 | 2 | magnetite | |
| TFA | 1000 | 2 | magnetite | |

EXAMPLE 4

Relationship Between Surfactant Concentration and Particle Size

A third set of experiments was carried out under similar conditions, but focused on three surfactants in more detail, viz., FeACAC (added as a 0.5% stock solution), PMCP (added as a 1% stock solution), and TFA (added as a 1% stock solution). These experiments are summarized in the following table.

TABLE 3

Effect of Fe-acac, PMCP, and TFA Surfactants on Nanoparticle Product

| Surfactant | Concentration, ppm | Innoculation |
|---|---|---|
| FeACAC | 100 | 1 mL of 0.5% |
| FeACAC | 100 | 1 mL of 0.5% |
| FeACAC | 100 | 1 mL of 0.5% |
| FeACAC | 500 | 5 mL of 0.5% |
| FeACAC | 500 | 5 mL of 0.5% |
| FeACAC | 500 | 5 mL of 0.5% |
| FeACAC | 1000 | 10 mL of 0.5% |
| FeACAC | 1000 | 10 mL of 0.5% |
| FeACAC | 1000 | 10 mL of 0.5% |
| PMCP | 100 | 0.5 mL of 1% |
| PMCP | 100 | 0.5 mL of 1% |
| PMCP | 100 | 0.5 mL of 1% |

TABLE 3-continued

Effect of Fe-acac, PMCP, and TFA Surfactants on Nanoparticle Product

| Surfactant | Concentration, ppm | Innoculation |
|---|---|---|
| PMCP | 500 | 2.5 mL of 1% |
| PMCP | 500 | 2.5 mL of 1% |
| PMCP | 500 | 2.5 mL of 1% |
| PMCP | 1000 | 5 mL of 1% |
| PMCP | 1000 | 5 mL of 1% |
| PMCP | 1000 | 5 mL of 1% |
| TFA | 100 | 0.5 mL of 1% |
| TFA | 100 | 0.5 mL of 1% |
| TFA | 100 | 0.5 mL of 1% |
| TFA | 500 | 2.5 mL of 1% |
| TFA | 500 | 2.5 mL of 1% |
| TFA | 500 | 2.5 mL of 1% |
| TFA | 1000 | 5 mL of 1% |
| TFA | 1000 | 5 mL of 1% |
| TFA | 1000 | 5 mL of 1% |

Figure 3:
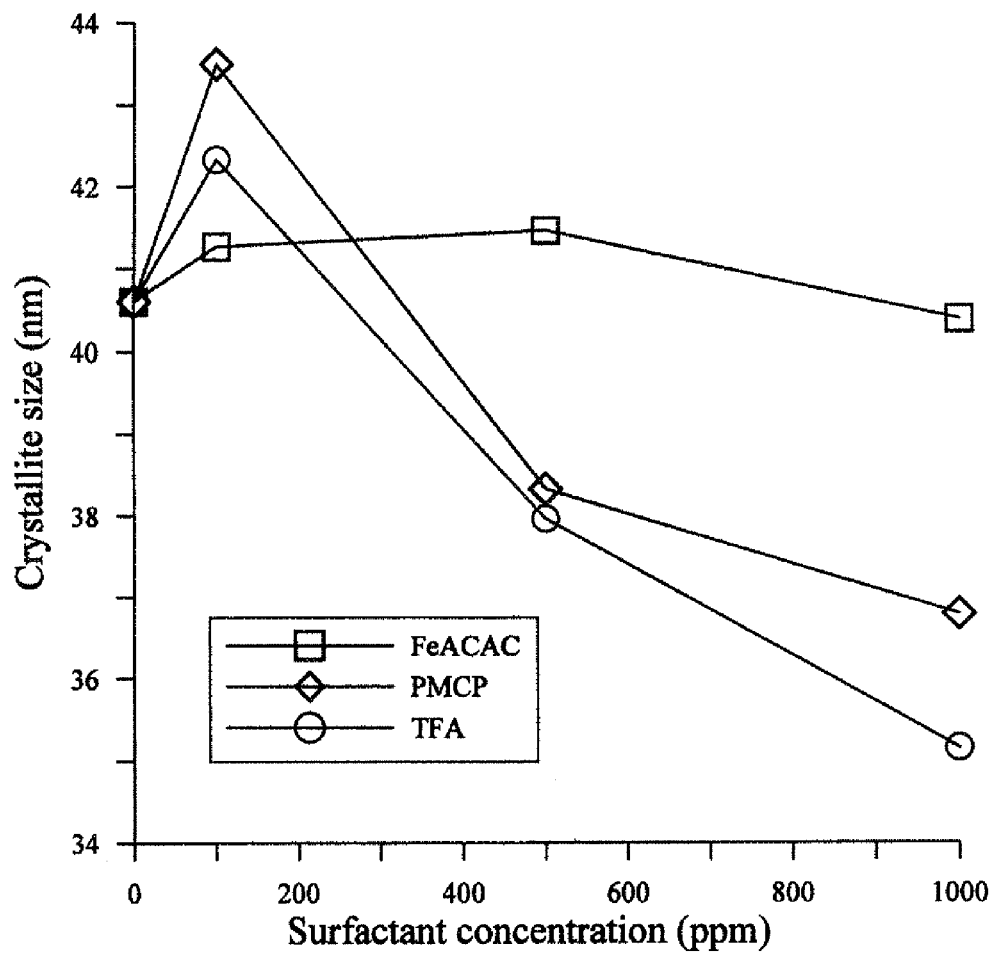
FIG. 3. A graph showing variation of crystallite size with surfactant concentration for three selected surfactants.

The results of particle size measurements on the product phases listed in the above table are presented graphically in FIG. 3, where it can be seen that there is a generally inverse relationship between surfactant concentration and particle size. It can also be seen that for this combination of bacteria and product composition, PMCP and TFA are significantly more effective than FeACAC in reducing particle size. These results also show that surfactant concentrations as high as 1000 ppm are well-tolerated and that the influence of the surfactant generally becomes more noticeable above a concentration around 200 ppm.

EXAMPLE 5

Processing Methods

Figure 4:
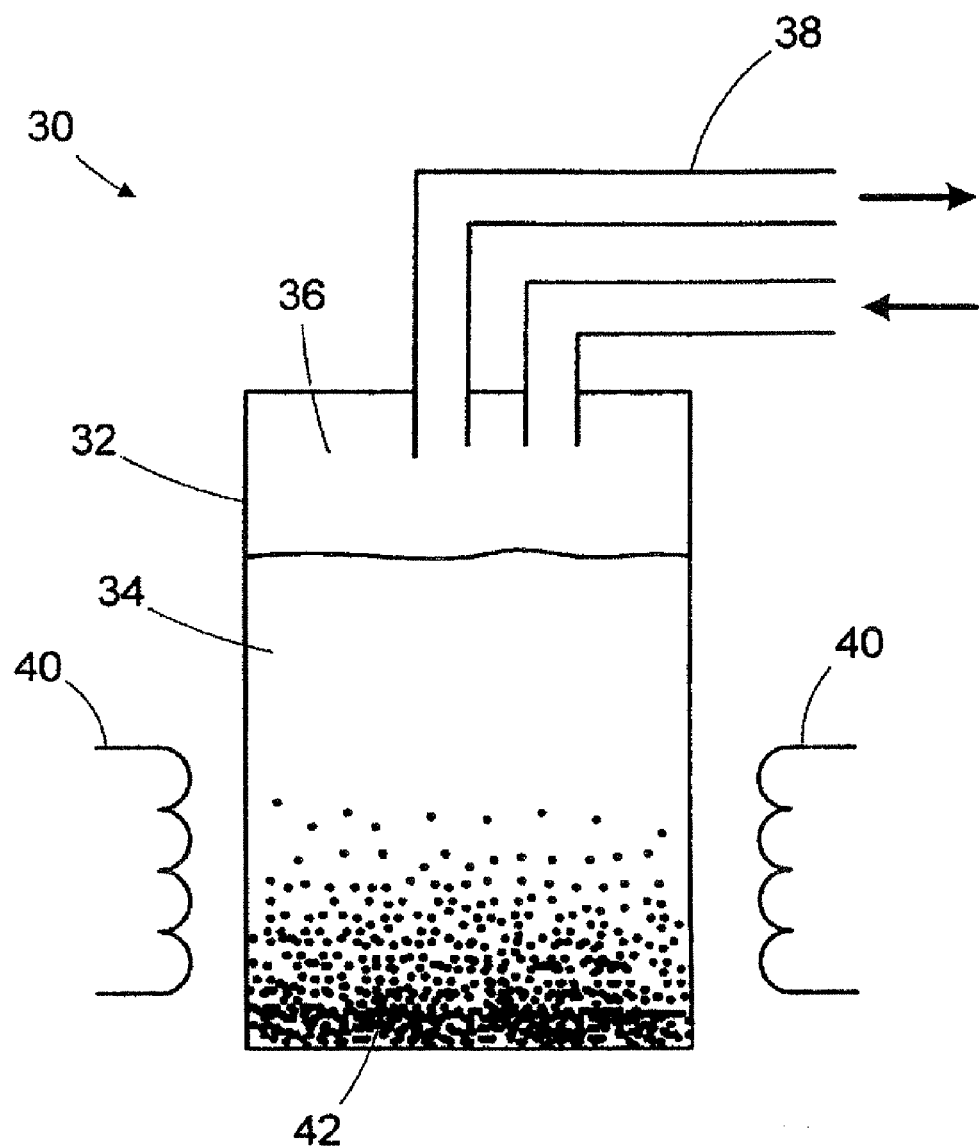
FIG. 4. Depiction of a preferred batch-type reactor useful for the described method.

FIG. 4 is a simplified diagram of a preferred batch-type bioprocessing reactor 30 suitable for carrying out the inventive process shown in FIG. 1. The reactor includes a container 32 constructed of glass or other inert material. A culture medium 34 is introduced in the container 32. The culture medium 34 contains an aqueous solution of nutrients, trace elements, vitamins, and other organic and inorganic compounds, and further contains at least one surfactant as described in the foregoing examples. The particular solutions described above are provided for illustrative purposes. Other solution constructs are possible, depending on the specific implementation.

The container 32 is preferably sealed to prevent the entry of air into the headspace gas region 36, thereby maintaining anaerobic conditions within the culture as well as permitting the inventive process to be carried out at pressures greater or less than ambient, if desired. A gas conduit 38 is preferably included to allow the introduction of selected gases into the container and to allow gases to exit the container. It will be appreciated that multiple gas inlets may be provided, and one or more gas inlets may be configured to enter the bottom of the fermenter or otherwise inject gas below the surface of the culture medium in order to enhance gas exchange. For the case of anaerobic thermophilic bacteria, a heating element 40 is preferably provided proximate to the container 32 to maintain the culture medium 34 at a desired temperature. An electron donor is introduced into the culture either as a gas (such as hydrogen or CO) via the gas conduit 38, or as a soluble species added anaerobically into the culture medium 34 (e.g., in the case of simple organics such as glucose, formate, acetate, lactate, and pyruvate). An electron acceptor containing one or more reducible transition elements, e.g., Fe(III), Cr(VI), Co(III), Ni(III), Mn(IV), or U(VI), is then suspended in the culture medium 34. One or more additional dopant metal species, which may or may not be reducible, may be incorporated in the suspended phase in the culture medium 34. If the dopant species is not reducible, it is generally present at a lower concentration than the reducible species. Exemplary dopant metals may include reducible or non reducible metals, such as Fe(III), Cr(VI), Co(III), Ni(III), Mn(IV), U(VI), Ni(II), Al(III), Zn(II), Mg(II), Mn(II), Cu(II), Co(II), and Pd(II).

In a particular embodiment, especially suitable for using *Thermoanaerobacter* sp. strain TOR-39, the pH is maintained at a level between about 6.9 and 7.5, and the solution is maintained at a temperature of between about 45° C. and 75° C. Specific temperature and pH may be varied to optimize product yield, and the optimum values depend on factors including the particular mixed oxide being formed and the particular bacterial strain being used. A surfactant concentration generally less than 1000 mg/L, and preferably less than about 300 mg/L, is added to the culture medium 34. It will be appreciated that the most effective surfactant concentration will be one at which surfactant molecules can effectively cover the surfaces of the metal oxide particles.

A crystalline product 42 forms in the container 32 as the bacteria reduce the reducible species. Any dopant species present in the solid precursor phase (feedstock), is typically retained in the major crystalline product 42 (e.g., $Fe_3O_4$), created by the reduction of the major metal species. When a sufficient quantity of crystalline product 42 has been produced and allowed to settle to the bottom of the container 32, the culture medium 34 is decanted and the crystalline product 42 is collected and washed. Container 32 may optionally be fitted with a drain valve (not shown) to allow the sold product to be removed without decanting the medium or breaking the gas seals. The incubation may be between 3 and 30 days, depending on the amount and size of the crystalline product desired.

Figure 5:
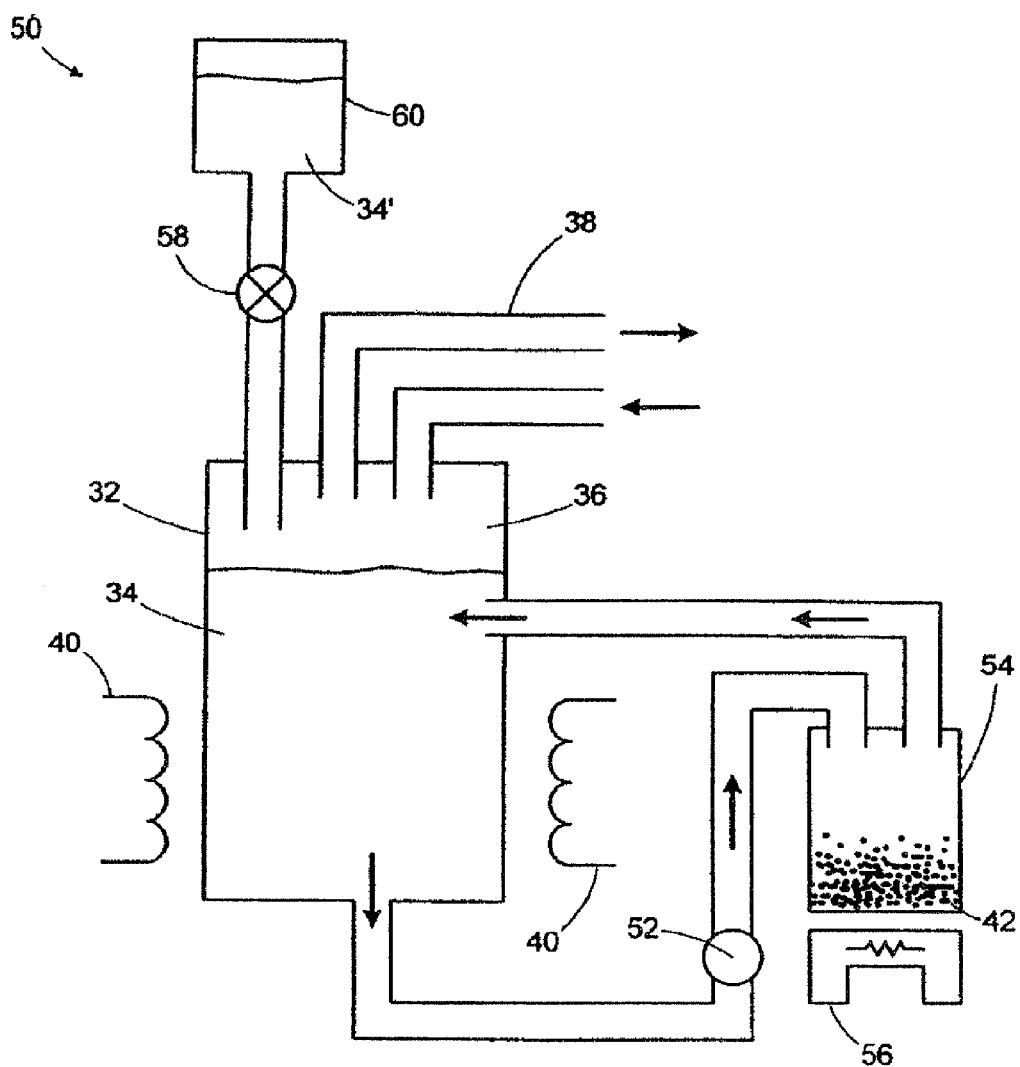
FIG. 5. Depiction of a continuous-type reactor useful for the described method.

The disclosed process may also be performed in a continuous arrangement as shown schematically by the bioreactor 50 of FIG. 5. The bioreactor 50 operates in a similar manner as the bioreactor 30 of FIG. 4. The bioreactor 50 includes a fluid recirculator 52 that allows the culture medium 34 to pass through an external trap 54 from which the crystalline product 42 can be removed. The trap 54 may separate the crystalline product 42 from the circulating culture medium by settling, due to the greater density of the crystalline product 42. If the crystalline product 42 is magnetic, the collection process can be assisted by using an electromagnet 56 or other suitable field-producing device to provide a magnetic field gradient in the trap 54.

Continuous collection of product from the circulating fluid may also be used as a farther means of controlling particle size (in addition to the size control afforded by the surfactant), because the particles tend to grow larger the longer they remain in the culture. It will be appreciated that to the extent a particular surfactant increases the rate at which particles may be shed from the bacterial surface, fluid circulation and surfactant additions may have a synergistic effect. An additional fluid valve 58 may be provided through which additional culture medium or nutrients 34 may be added from an external reservoir 60 while maintaining the anaerobic conditions within the container 32. While there have been shown and described what are at present considered the preferred embodiments of the invention, those skilled in the art may make various changes and modifications which remain within the scope of the invention defined by the appended claims.

What is claimed is:

1. A method for producing metal oxide nanoparticles, the method comprising:
   (i) subjecting a combination of reaction components to conditions conducive to microbial-mediated formation of metal oxide nanoparticles, wherein said combination of reaction components comprises: metal-reducing microbes; a culture medium suitable for sustaining said metal-reducing microbes; trifluoroacetic acid in a concentration of at least 200 mg/L and up to 1000 mg/L that achieves separation of said metal oxide particles from said metal-reducing microbes; a reducible metal oxide component containing at least one reducible metal species; and at least one electron donor that provides donatable electrons to said metal-reducing microbes during consumption of the electron donor by said metal-reducing microbes, to form metal oxide nanoparticles detached from said metal-reducing microbes, wherein said metal oxide nanoparticles contain a reduced form of said reducible metal oxide component; and
   (ii) isolating said metal oxide nanoparticles from other reaction components.

2. The method of claim 1 wherein said at least one electron donor comprises one or more carboxylate-containing compounds that can be oxidatively consumed by the microbes.

3. The method of claim 1 wherein said at least one electron donor comprises one or more sugar compounds that can be oxidatively consumed by the microbes.

4. The method of claim 1 wherein said at least one electron donor comprises one or more oxidizable gaseous compounds or elements that can be oxidatively consumed by the microbes.

5. The method of claim 1 wherein the reducible metal component comprises Fe(III) oxyhydroxide.

6. The method of claim 1 wherein at least 90% of the metal oxide nanoparticles are within a size range spanning 500 nm from minimum to maximum diameter.

7. The method of claim 1 wherein at least 90% of the metal oxide nanoparticles are within a size range spanning 200 nm from minimum to maximum diameter.

8. The method of claim 1 wherein the metal oxide nanoparticles possess a size within a range of about 2 nm to about 500 nm.

9. The method of claim 1 wherein the metal oxide nanoparticles possess a size within a range of about 2 nm to about 200 nm.

10. The method of claim 1 wherein the metal oxide nanoparticles possess a size within a range of about 2 nm to about 100 nm.

11. The method of claim 1 wherein said metal oxide nanoparticles possess a spinel-type structure having the formula:

$$M'_x M''_{3-x} O_4 \quad (1)$$

wherein M' and M'' are the same or different metal cations, at least one being a transition metal cation, and x is a numerical value of 0.01 to 1.5.

12. The method of claim 11 wherein M' and M'' are selected from transition metal cations, and the reducible metal component includes said transition metal cations.

13. The method of claim 11 wherein M' and M'' are selected from first-row transition metal cations, and the reducible metal component includes said first-row transition metal cations.

14. The method of claim 1 wherein said reducible metal oxide component comprises at least Fe(III)-containing compound or material.

15. The method of claim 14 wherein the metal oxide nanoparticles possess a spinel-type structure having the formula:

$$M'_y Fe_{3-y} O_4$$

wherein M' is a metal cation and y is a numerical value of 0.01 to 2.

16. The method of claim 15 wherein M' is a transition metal.

17. The method of claim 15 wherein M' is a first-row transition metal.

18. The method of claim 1 wherein said metal-reducing microbes are thermophilic, and said method is conducted at a temperature of at least 40° C.

19. The method of claim 1 wherein said metal-reducing microbes are mesophilic or psychrotolerant, and said method is conducted at a temperature of less than 40° C.

20. The method of claim 1 wherein the metal-reducing microbes are metal-reducing bacteria.

21. The method of claim 1, wherein said isolating step (ii) comprises:
   (ii) precipitating said metal oxide nanoparticles; and
   (iii) separating said metal oxide nanoparticles from other reaction components.

* * * * *